United States Patent
Enomoto

(10) Patent No.: US 11,430,573 B2
(45) Date of Patent: Aug. 30, 2022

(54) PATIENT MONITORING SYSTEM

(71) Applicant: NIHON KOHDEN CORPORATION, Tokyo (JP)

(72) Inventor: Yoshinori Enomoto, Tokorozawa (JP)

(73) Assignee: NIHON KOHDEN CORPORATION, Toyko (JP)

( * ) Notice: Subject to any disclaimer, the term of this patent is extended or adjusted under 35 U.S.C. 154(b) by 216 days.

(21) Appl. No.: 16/824,848

(22) Filed: Mar. 20, 2020

(65) Prior Publication Data
US 2020/0312451 A1 Oct. 1, 2020

(30) Foreign Application Priority Data
Mar. 26, 2019 (JP) .............................. JP2019-058291

(51) Int. Cl.
| | |
|---|---|
| G06F 3/06 | (2006.01) |
| G11B 20/10 | (2006.01) |
| G16H 40/67 | (2018.01) |
| G16H 15/00 | (2018.01) |
| G06F 3/14 | (2006.01) |
| G06F 16/71 | (2019.01) |
| G16H 10/60 | (2018.01) |

(52) U.S. Cl.
CPC .............. *G16H 40/67* (2018.01); *G06F 3/14* (2013.01); *G06F 16/71* (2019.01); *G16H 10/60* (2018.01); *G16H 15/00* (2018.01)

(58) Field of Classification Search
CPC ........ G16H 40/67; G16H 10/60; G16H 15/00; G06F 3/14; G06F 16/71; G09G 2358/00; G09G 5/39; G09G 2360/128; G09G 2380/08
See application file for complete search history.

(56) References Cited

U.S. PATENT DOCUMENTS

| | | | |
|---|---|---|---|
| 6,761,312 B2 | 7/2004 | Piatek et al. | |
| 8,874,035 B2 | 10/2014 | Sherman et al. | |
| 2006/0204047 A1 | 9/2006 | Dave et al. | |
| 2009/0054735 A1* | 2/2009 | Higgins | A61B 5/0006 600/300 |
| 2013/0300846 A1* | 11/2013 | Miller | A61B 1/04 348/65 |
| 2014/0266709 A1 | 9/2014 | Nagase et al. | |
| 2016/0260417 A1* | 9/2016 | Asai | G09G 5/363 |

FOREIGN PATENT DOCUMENTS

| | | |
|---|---|---|
| JP | 2014-171776 A | 9/2014 |
| WO | 2015-125906 A1 | 8/2015 |

* cited by examiner

*Primary Examiner* — Maroun P Kanaan
(74) *Attorney, Agent, or Firm* — Pearne & Gordon LLP

(57) ABSTRACT

A patient monitoring system includes: a display configured to display, only for a first period, information including changes over time in physiological information acquired from at least one patient; a first storage configured to store, only for a second period longer than the first period, data corresponding to the information displayed on the display; a second storage having a storage capacity different from a storage capacity of the first storage; a user interface configured to receive a data preservation instruction from a user; and one or more processors configured to store in the second storage at least a part of the data that has been in the first storage before the user interface receives the data preservation instruction.

13 Claims, 5 Drawing Sheets

PATIENT MONITORING SYSTEM

CROSS-REFERENCE TO RELATED APPLICATIONS

This application is based on and claims priority under 35 USC 119 from Japanese Patent Application No. 2019-058291 filed on Mar. 26, 2019, the contents of which are incorporated herein by reference.

The presently disclosed subject matter relates to a system for monitoring physiological information of subjects.

BACKGROUND

Japanese Patent Application Laid-Open No. 2014-171776 discloses an example of a patient monitoring system including bedside monitors and a central monitor. The bedside monitors are placed near patients with sensors to manage physiological information of the patients. The central monitor is placed in a nurse station or the like to centrally manage physiological information of a plurality of patients. In the following description, bedside monitors and central monitors will be referred to collectively as patient monitors when needed.

Sensors for acquiring physiological information are attached to each patient. Physiological information acquired through the sensors is transmitted to at least one of the bedside monitor and the central monitor by at least one of cable communication and wireless communication. The at least one of the bedside monitor and the central monitor performs a predetermined analyzing process and a display process on the received physiological information. The at least one of the bedside monitor and the central monitor has a storage for storing data corresponding to the physiological information. If the amount of stored data reaches the upper limit of the capacity of the storage, old data is automatically deleted, sequentially from the oldest data.

In the event of a medical accident, Japanese medical accident investigation system demands preservation and provision of data stored in a storage at that time. If the preserved data is provided, the data is analyzed to attempt to reproduce the situation at the time of the accident and determine the cause of the accident.

However, preserving and providing data demands special software tools and knowledge, and in order to performing the task smoothly, a skill is demanded. If the task requires a long time, in the middle of the task, the amount of data stored in the storage may reach the upper limit of the capacity of the storage, and some data may be deleted.

The presently disclosed subject matter is provided with patient monitoring system to make it easy to reproduce a situation in the case where the situation is the cause of a demand for preservation of data related to patient monitoring.

SUMMARY

A patient monitoring system of a first aspect includes: a display configured to display, only for a first period, information including changes over time in physiological information acquired from at least one patient; a first storage configured to store, only for a second period longer than the first period, data corresponding to the information displayed on the display; a second storage having a storage capacity different from a storage capacity of the first storage; a user interface configured to receive a data preservation instruction from a user; and one or more processors configured to store in the second storage at least a part of the data that has been in the first storage before the user interface receives the data preservation instruction.

A patient monitoring system of a second aspect includes: a display configured to display information including changes over time in physiological information acquired from at least one patient; a storage; and one or more processors configured to start to store, in the storage, video data indicating changes over time in images displayed on the display when the display is activated.

DESCRIPTION OF EMBODIMENTS

Hereinafter, examples of embodiments will be described in detail with reference to the accompanying drawings. The individual drawings have scales appropriately determined such that individual elements to be described have recognizable sizes.

Figure 1:
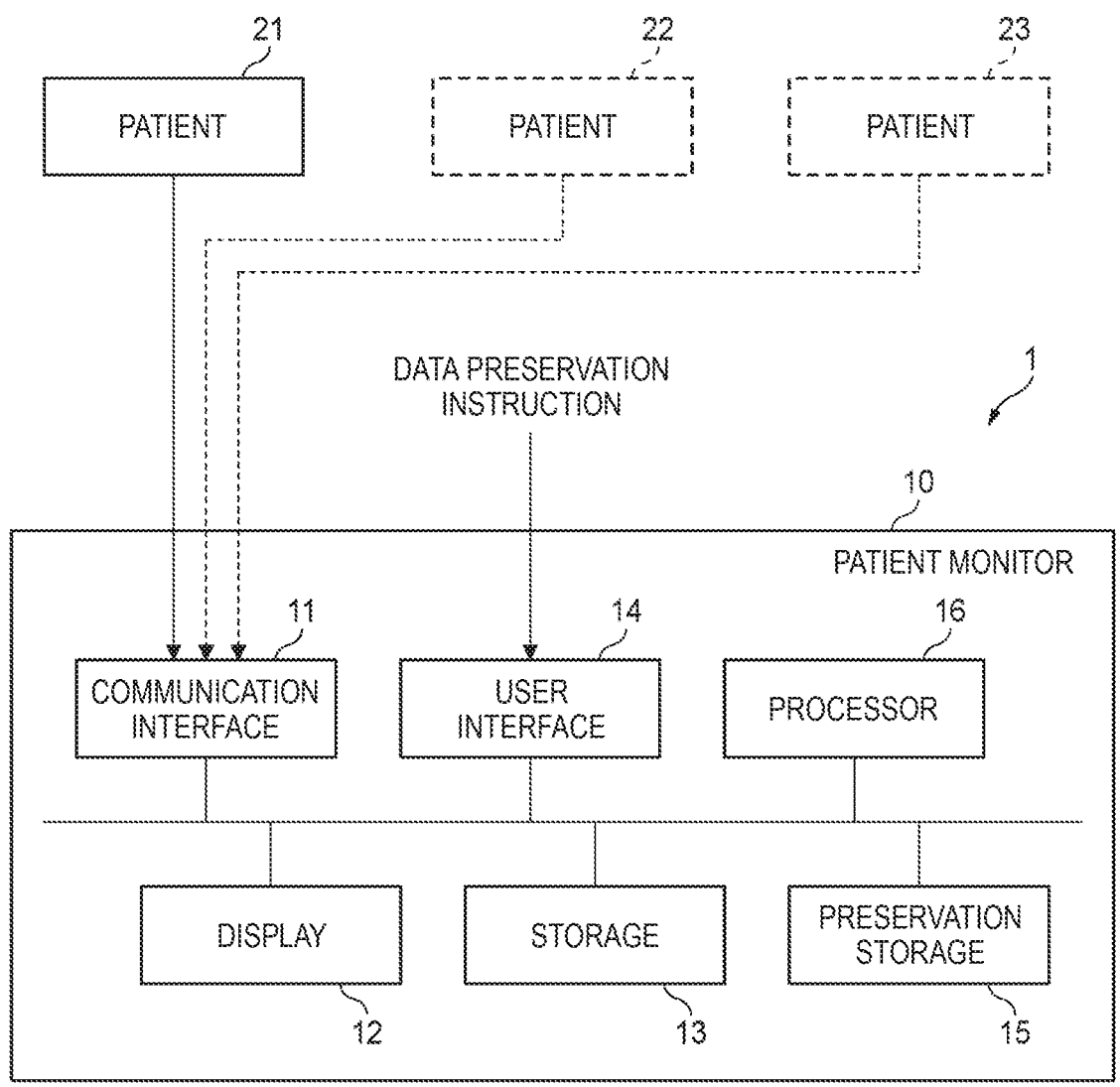
FIG. 1 illustrates the configuration a patient monitoring system according to an embodiment.
Figure 2:
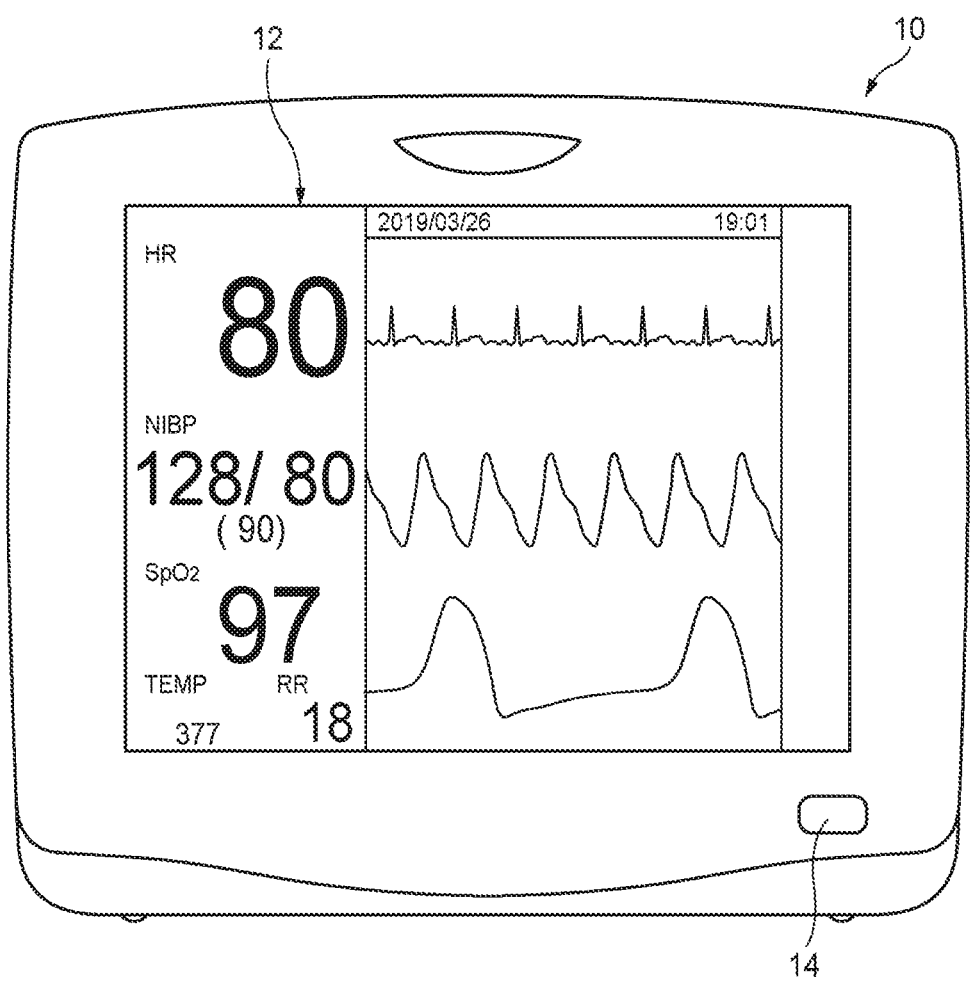
FIG. 2 illustrates the external appearance of a bedside monitor as an example of patient monitors.

FIG. 1 illustrates the configuration of a patient monitoring system 1 according to an embodiment. The patient monitoring system 1 can include a patient monitor 10. For example, the patient monitor 10 may be a bedside monitor as illustrated in FIG. 2. The bedside monitor is a device which is deployed near a patient 21 to acquire physiological information of the patient 21 through sensors (not illustrated in the drawings) attached to the patient 21. As examples of physiological information, heart rate, blood pressure, the arterial oxygen saturation, the concentration of carbon dioxide in exhaled air, electrocardiograms, electroencephalograms, and so on can be taken.

As illustrated in FIG. 1, the patient monitor 10 can include a communication interface 11. The sensors attached to the patient 21 output sensor signals corresponding to the detected physiological information. The communication interface 11 receives the sensor signals.

The patient monitor 10 can include a display 12. As illustrated in FIG. 2, on the display 12, a variety of information can be displayed. As examples of such information, information identifying the patient 21, information representing changes over time in the physiological information acquired through the sensors, information notifying abnormalities of the corresponding physiological information, setting information of the patient monitor 10, and so on can be taken. Changes in physiological information over time may be displayed in a wave form or in numbers.

Figure 3A:
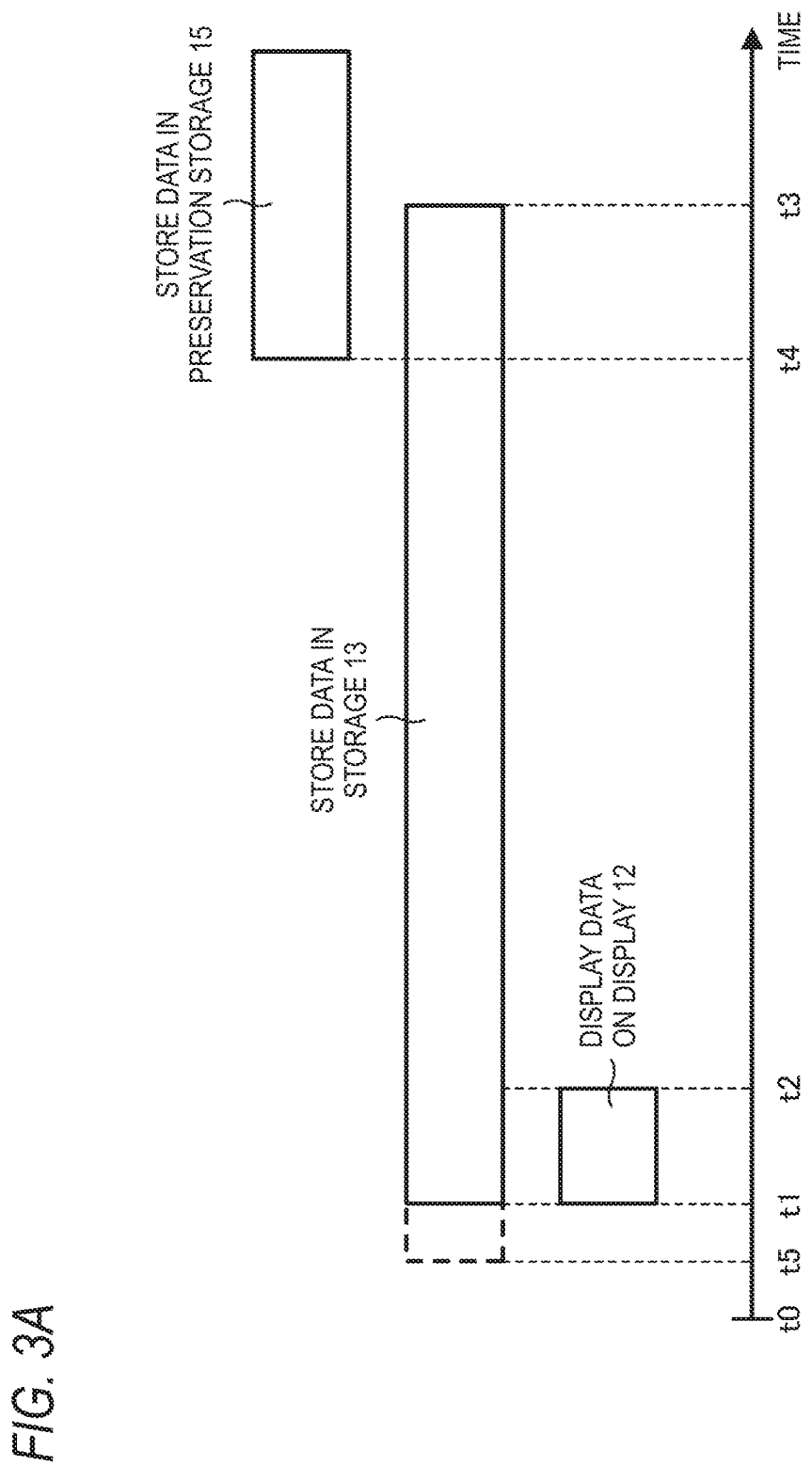
FIG. 3A illustrates an operation of the patient monitoring system.

FIG. 3A is a view for explaining various processes which are performed on data corresponding to physiological information. Data corresponding to the physiological information is generated at a time point t0. At a time point t1, a process of displaying the corresponding data on the display 12 is performed. Only for a period from the time point t1 to a time point t2, the corresponding data is displayed on the display 12. The corresponding period can be appropriately changed through the display setting of the patient monitor 10. The period from the time point t1 to the time point t2 is an example of a first period.

As illustrated in FIG. 1, the patient monitor 10 can include one or more storages as a storage 13. The storage 13 is a device for storing data corresponding to the information displayed on the display 12. The storage 13 can be realized with hard disk drive devices, semiconductor memories, magnetic tape devices, and so on. The storage 13 is an example of a first storage.

As illustrated in FIG. 3A, the storage 13 is configured to store data corresponding to the information displayed on the display 12 only for a period from the time point t1 to a time point t3. In other words, the data which is stored in the storage 13 can include not only the information identifying the patient 21 and information representing changes over time in the physiological information of the patient 21, but also information notifying abnormalities of the physiological information, the setting information of the patient monitor 10, and so on. The period from the time point t1 to the time point t3 is an example of a second period. The second period is longer than the first period.

If the amount of data stored in the storage 13 reaches the upper limit of the storage capacity of the storage 13, old data is automatically deleted, sequentially from the oldest data. The second period corresponds to a period from when certain data is stored to when the stored data is deleted, in the case where data is consecutively stored in the storage 13.

Figure 3B:
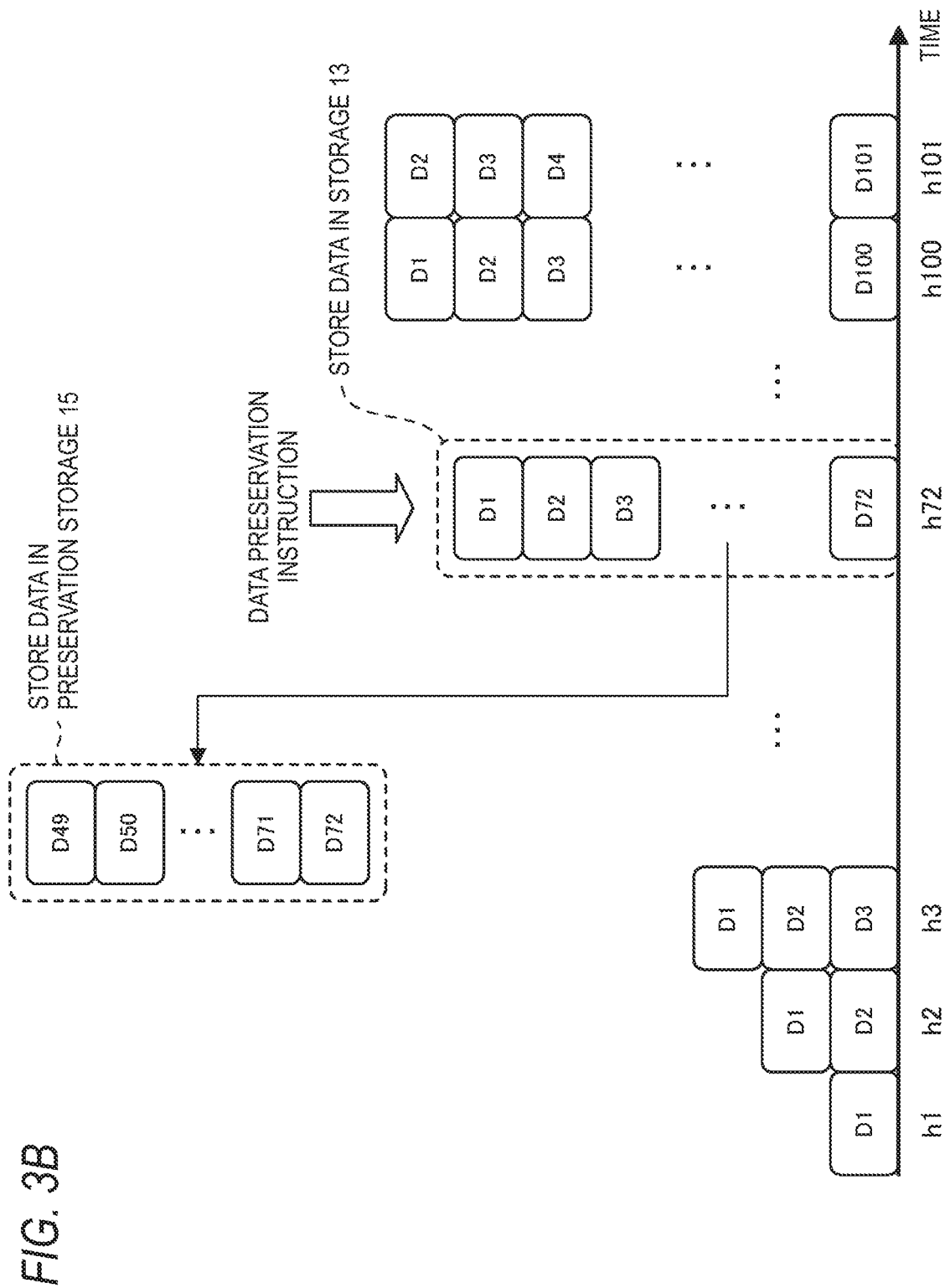
FIG. 3B illustrates an operation of the patient monitoring system.

FIG. 3B schematically illustrates the state of data stored in the storage 13. A reference symbol "D1" represents a data set stored in the storage 13 for the first one hour from the time point t1. A reference symbol "D2" represents a data set stored in the storage 13 for the next one hour. A reference symbol "DN" represents a data set stored in the storage 13 for a period from a time point after (n−1) hours from the time point t1 to a time point after n hours from the time point t1.

In this example, the second period is set to 100 hours. In other words, if data sets D1 to D100 are stored, the amount of stored data reaches the upper limit of the capacity of the storage 13. Therefore, after 100 hours pass from the time point t1, while a data set D101 is stored, the data set D1 is deleted. In order to facilitate explanation, the example in which date deletion is performed in units of a data set which is defined in units of one hour has been described. However, individual data items constituting data sets can be sequentially deleted from the storage 13 if 100 hours pass (in other words, when the time point t3 comes).

As illustrated in FIG. 1, the patient monitor 10 can include a user interface 14. The user interface 14 is configured to receive a data preservation instruction from a user. The data preservation instruction is an instruction for performing data preservation demanded for the accuracy of medical accident investigation in the event of a medical accident or the like.

In the example illustrated in FIG. 2, the user interface 14 is provided as a dedicated button switch provided on the housing of the bedside monitor. In the case where data preservation is necessary, the user pushes the button switch. In the case where the display 12 has a touch panel function, the user interface 14 may be an image which is displayed on the display 12 and can be operated by a touch (a so-called software key). Alternatively, the user interface 14 may be a voice recognition interface or a gesture recognition interface. In this case, the user says specific words or makes a specific gesture, which the user interface 14 recognizes.

As illustrated in FIG. 1, the patient monitor 10 can include one or more storages as a preservation storage 15. The preservation storage 15 is a device for preserving data which is objects of data preservation instructions. The storage capacity of the preservation storage 15 is smaller than the storage capacity of the storage 13. The preservation storage 15 can be realized with hard disk drive devices, semiconductor memories, magnetic tape devices, and so on. The preservation storage 15 may be provided as a part of a storage medium which is used as the storage 13 (a separate area defined by partition), or may be configured as a portable storage which can be installed in and removed from the patient monitor 10, independently from the storage 13. The preservation storage 15 is an example of a second storage.

The patient monitor 10 can include one or more processors as a processor 16. As illustrated in FIG. 3B, the processor 16 is configured to store in the preservation storage 15 at least a part of data stored in the storage 13 before reception of a data preservation instruction by the user interface 14.

In the example of FIG. 3B, a data preservation instruction is issued after elapse of 72 hours from the time point t1. In response to this instruction, a part of the data stored in the storage 13, i.e. the data sets D49 to D72 stored for 24 hours before the corresponding time point are stored in the preservation storage 15. As illustrated in FIG. 3A, in response to a data preservation instruction received at a time point t4, specific data included in the above-mentioned data sets is stored in the preservation storage 15. The data stored in the preservation storage 15 is not be deleted even though the second period passes.

According to this configuration, if the user inputs a data preservation instruction to the user interface 14 when needed, data preservation based on the demand of the medical accident investigation system is automatically performed. Since special software and knowledge for taking data from storage 13 are not necessary, and data preservation is easily and smoothly performed, the possibility that it is possible to avoid data from being deleted due to expiration of the storage period of the storage 13 increases. Furthermore, since the data which is stored in the preservation storage 15 includes not only the information identifying the patient 21 and the information representing changes over time in the physiological information on the patient 21, but also other information given to be displayed on the display 12 (such as alarm information representing abnormalities of the physiological information, event information, time information, and the setting information of the patient monitor 10), it becomes easy to reproduce the situation which is the cause of the demand for preservation of the data.

The processor 16 having the above-described function can be realized with a general-purpose microcomputer which operates in cooperation with general-purpose memories. As examples of the general-purpose microcomputer, CPUs and MPUs can be taken. As examples of the general-purpose memories, RAMs and ROMs can be taken. In this case, on a ROM, a computer program for performing the above-described process may be stored. The processor 16 designates at least a part of the computer program stored in the ROM, and develops the designated part in the RAM, and performs the above-described process in cooperation with the RAM. A part of the storage 13 may be used as such a general-purpose memory. The processor 16 may also serve as a processor for displaying data on the display 12 and storing data in the storage 13. The processor 16 may be realized with dedicated integrated circuits, such as microcontrollers, ASICs, and FPGAs, capable of executing the computer program for implementing the above-mentioned process. The processor 16 may be realized with a combination of general-purpose microprocessors and dedicated integrated circuits.

The data which is stored in the storage 13 may be video data representing changes over time in images displayed on the display 12.

According to this configuration, since it is possible to visually check changes in the situation which is displayed on the display 12, it becomes easier to specify the cause of the demand for data preservation.

As illustrated in FIG. 3A, storing of the data corresponding to the physiological information in the storage 13 may automatically start at a time point t5 when the display 12 is activated. In other words, before display of the data corresponding to the physiological information of the patient 21 starts, storing of the data to be preserved starts.

According to this configuration, information on the operation settings of the patient monitor and information on the environment around the patient 21 also may be stored in the storage 13. In this case, the possibility that it will be easy to specify the cause of the demand for data preservation increases. This configuration is especially useful in the case where the data stored in the storage 13 is video data representing changes over time in images displayed on the display 12.

Figure 4:
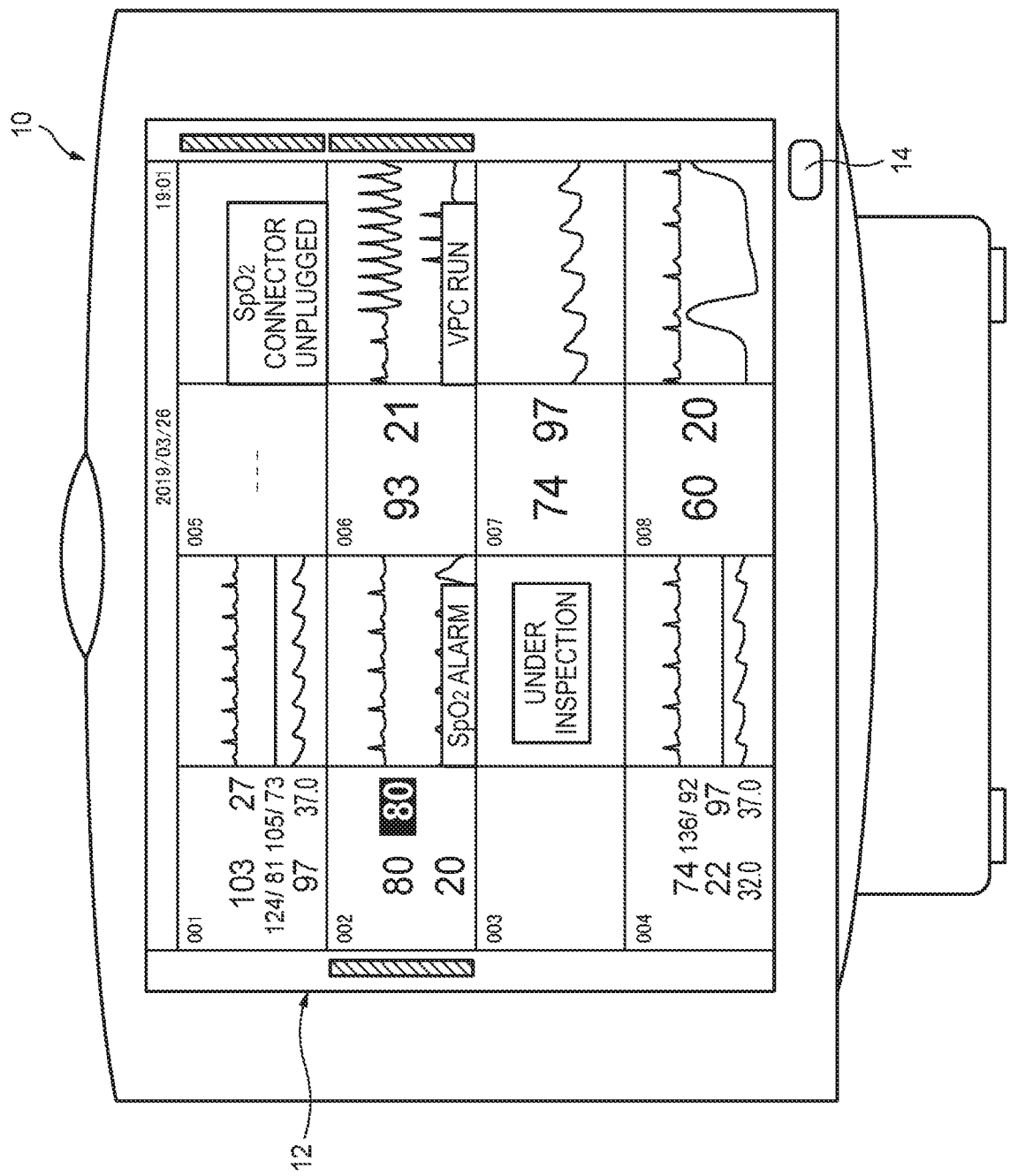
FIG. 4 illustrates the external appearance of a central monitor as another example of patient monitors.

As illustrated in FIG. 4, the patient monitor 10 may be a central monitor. The central monitor is a device which is deployed in a nurse station or the like to centrally manage physiological information of a plurality of patients.

In this case, as illustrated in FIG. 1, the communication interface 11 receives sensor signals from each of the plurality of patients. In FIG. 1, as an example of the plurality of patients, three patients 21 to 23 are illustrated.

In this case, on the display 12, a variety of information on each of the plurality of patients is displayed. As examples of such information, information representing each patient, information representing changes over time in physiological information acquired through the sensors attached to each patient, information notifying abnormalities of the corresponding physiological information, the setting information of each of bedside monitors associated with the patients, the setting information of the central monitor, and so on can be taken. Changes in physiological information over time may be displayed in a wave form or in numbers.

Storing of data in the storage 13 is performed with respect to each patient. Since the storing method is as described with reference to FIG. 3A and FIG. 3B, repetitive descriptions will not be made.

Inputting of a data preservation instruction through the user interface 14 is performed after a patient for who preservation is demanded is designated. Patient designation and instruction confirmation are performed by operating dedicated button switches provided on the housing of the central monitor. In the case where the display 12 has a touch panel function, patient designation and instruction confirmation may be performed through images which are displayed on the display 12 and can be operated by touches. Alternatively, patient designation and instruction confirmation may performed by making the user interface 14 recognize specific words or gestures.

If a data preservation instruction is input to the user interface 14, the processor 16 stores only at least a part of data stored in the storage 13 with respect to a patient designated by the corresponding instruction before the corresponding instruction, in the preservation storage 15.

Even according to this configuration, the same or similar effects as those described referring to the bedside monitor as an example are achieved.

Alternatively, in the case where a data preservation instruction is input to the user interface 14, the processor 16 may store data stored in the storage 13 with respect to all patients which are objects of monitoring of the central monitor, in the preservation storage. The case where the data stored in the storage 13 is video data representing changes over time in images displayed on the display 12 may become an example thereof.

According to this configuration, besides the situation of a patient for who data preservation is demanded, information on the environment around the patient (such as simultaneous occurrence of nurse calls, the whereabouts of health professionals, and so on) also may become objects of data preservation. In this case, with respect to the cause of a demand for data preservation, more detailed analysis can become possible.

A patient monitoring system of a first aspect includes: a display configured to display, only for a first period, information including changes over time in physiological information acquired from at least one patient; a first storage configured to store, only for a second period longer than the first period, data corresponding to the information displayed on the display; a second storage having a storage capacity different from a storage capacity of the first storage; a user interface configured to receive a data preservation instruction from a user; and one or more processors configured to store in the second storage at least a part of the data that has been in the first storage before the user interface receives the data preservation instruction.

According to the patient monitoring system of the first aspect, if the user inputs a data preservation instruction to the user interface when needed, data preservation based on the demand of the medical accident investigation system is automatically performed. Since special software and knowledge for taking data from the first storage are not necessary, and data preservation is easily and smoothly performed, the possibility that it is possible to avoid data from being deleted due to expiration of the second period increases. Since the data which is stored in the second storage includes not only information identifying the patient and information on changes over time in the physiological information of the patient, but also other information given to be displayed on the display (such as times, alarms, events, and so on), it becomes easy to reproduce the situation which is the cause of the demand for preservation of the data.

A patient monitoring system of a second aspect includes: a display configured to display information including changes over time in physiological information acquired from at least one patient; a storage; and one or more processors configured to start to store, in the storage, video data indicating changes over time in images displayed on the display when the display is activated.

According to the patient monitoring system of the second aspect, since it is possible to visually check change in the situation which is displayed on the display, it becomes easy to specify the cause of the demand for data preservation. Before display of the data corresponding to the physiological information of the patient starts, storing of the data to be preserved starts. Therefore, the environment around the patient also may be stored in the storage without being lost. In this case, the possibility that it will be easy to specify the cause of the demand for data preservation increases.

The above-described embodiment is merely an example for facilitating understanding of the presently disclosed subject matter. The configuration according to the above-described embodiment can be appropriately modified and changed without departing from the gist of the presently disclosed subject matter.

In the above-described embodiment, the storage 13, the preservation storage 15, and the processor 16 are disposed inside the housing of the patient monitor 10 having the display 12. However, at least one of the storage 13, the preservation storage 15, and the processor 16 may be disposed inside a remote control device capable of communication with the communication interface 11 of the patient monitor 10 through communication networks.

What is claimed is:

1. A patient monitoring system comprising:
    a display configured to display, only for a first period, information including changes over time in physiological information acquired from at least one patient;
    a first storage configured to store, only for a second period longer than the first period, data corresponding to the information displayed on the display;
    a second storage having a storage capacity different from a storage capacity of the first storage;
    a user interface configured to receive a data preservation instruction from a user; and
    one or more processors configured to store in the second storage at least a part of the data that has been in the first storage before the user interface receives the data preservation instruction, wherein:
    the one or more processors are configured to delete the data from the first storage, when the second period elapses since storing in the first storage, and
    after storing the data in the second storage from the first storage, even when the second period elapses since storing in the first storage, the one or more processors are configured to keep the data stored in the second storage.

2. The patient monitoring system according to claim 1, wherein
    the data is video data representing changes over time in images displayed on the display.

3. The patient monitoring system according to claim 1, wherein
    storing of the data in the first storage automatically starts when the display is activated.

4. The patient monitoring system according to claim 1, wherein
    the physiological information acquired from each of a plurality of patients is collectively displayed on the display, and
    the user interface is capable of receiving the data preservation instruction with respect to at least one of the plurality of patients.

5. The patient monitoring system according to claim 1, wherein
    the second storage has the storage capacity smaller than the storage capacity of the first storage.

6. A patient monitoring system comprising:
    a display configured to display information including changes over time in physiological information acquired from at least one patient;
    a first storage;
    a second storage; and
    one or more processors configured to:
        start to store, in the first storage and prior to receipt of one or more instructions, video data indicating changes over time in images displayed on the display when the display is activated
        store, in the second storage, at least part of the video data that has been in the first storage when a period elapses,
        delete the video data from the first storage when the period elapses, and
        keep the video data in the second storage after storing the video data in the second storage from the first storage even when the period elapses.

7. The patient monitoring system according to claim 6, wherein
    the physiological information acquired from each of a plurality of patients is collectively displayed on the display.

8. The patient monitoring system according to claim 6, wherein
    storing of the data in the first storage automatically starts when the display is activated.

9. The patient monitoring system according to claim 6, further comprising a user interface that is configured to receive the one or more instructions.

10. The patient monitoring system according to claim 9, wherein
    the physiological information acquired from each of a plurality of patients is collectively displayed on the display, and
    the user interface is capable of receiving a first instruction with respect to at least one of the plurality of patients, the first instruction comprising a data preservation instruction selected from the one or more instructions.

11. The patient monitoring system according to claim 6, wherein
    the second storage has a first storage capacity that is different than a second storage capacity of the first storage.

12. The patient monitoring system according to claim 6, wherein
    the one or more instructions comprises at least one instruction for performing data preservation demanded for accuracy of an investigation.

13. The patient monitoring system according to claim 1, wherein
    the data preservation instruction comprises at least one instruction for performing data preservation demanded for accuracy of an investigation.

* * * * *